United States Patent [19]

Lowy et al.

[11] Patent Number: 5,716,620
[45] Date of Patent: Feb. 10, 1998

[54] SELF-ASSEMBLING RECOMBINANT PAPILLOMAVIRUS CAPSID PROTEINS

[75] Inventors: Douglas R. Lowy, Washington, D.C.; John T. Schiller, Silver Spring; Reinhard Kirnbauer, Bethesda, both of Md.

[73] Assignee: The United States of America as represented by the Department of Health and Human Services, Washington, D.C.

[21] Appl. No.: 475,783

[22] Filed: Jun. 7, 1995

Related U.S. Application Data

[60] Division of Ser. No. 32,869, Mar. 16, 1993, Pat. No. 5,437,951, which is a continuation-in-part of Ser. No. 941,371, Sep. 3, 1992.

[51] Int. Cl.$^6$ ................................................. A61K 39/12
[52] U.S. Cl. ................................. 424/186.1; 424/204.1; 424/277.1; 435/69.3; 935/65
[58] Field of Search ........................ 424/186.1, 204.1, 424/277.1; 935/65; 536/23.72; 435/69.3

[56] References Cited

U.S. PATENT DOCUMENTS

| | | |
|---|---|---|
| 4,520,113 | 5/1985 | Gallo et al. |
| 4,551,270 | 11/1985 | Danos et al. |
| 4,748,109 | 5/1988 | Baird. |
| 4,777,239 | 10/1988 | Schoolnik et al. |
| 4,983,728 | 1/1991 | Herzog et al. |
| 5,039,607 | 8/1991 | Skold et al. |
| 5,045,447 | 9/1991 | Minson. |
| 5,057,411 | 10/1991 | Lancaster et al. |
| 5,071,757 | 12/1991 | Kreider et al. |
| 5,081,029 | 1/1992 | Starling et al. |
| 5,180,806 | 1/1993 | Dillner et al. |
| 5,186,933 | 2/1993 | Estes. |

FOREIGN PATENT DOCUMENTS

| | | |
|---|---|---|
| 0133123 | 7/1984 | European Pat. Off. |
| 9010459 | 9/1990 | WIPO. |
| WO 90/10867 | 9/1990 | WIPO. |
| 9118118 | 11/1991 | WIPO. |
| WO 91/18294 | 11/1991 | WIPO. |
| 9302184 | 2/1993 | WIPO. |
| 9400152 | 1/1994 | WIPO. |
| 9420137 | 9/1994 | WIPO. |

OTHER PUBLICATIONS

Baker, C.Sequence Analysis of Papillomavirus Genomes. The Papillomaviruses. 321–385 (1987).
Baker, T., et al. Structures of bovine and human papillomaviruses. Biophys. J. 60:1445–1456 (1991).
Bradley, L., et al. Selected methods in cellular immunology. In Vitro Immune Responses. 164–166 (1980).
Chen, E., et al. The primary structure and genetic organization . . . Nature. 299:529–534 (1982).
Christensen, N., et al. Monoclonal antibody-mediated neutralization of . . . J. of Virology. 64:5678–5687 (1990).
Christensen, N., et al. The open reading frame L2 of cottontail rabbit papillomavirus . . . Virology. 181:572–579 (1991).
Cowsert, L., et al. Topographical and conformational epitopes of bovine . . . J.Natl.Cancer Inst. 79:1053–1057 (1987).
Crawford, L., et al. A comparative study of polyoma and papilloma viruses. Virology 21:258–263 (1963).
Dvoretzky, I., et al. A quantitative in Vitro focus assay for bovine papilloma virus. Virology 103:369–375 (1980).
Ghim, S., et al. Comparison of neutralization of BPV-1 infection of C127 cells and . . . Int. J. Cancer 49:285–289 (1991).
Hartig, P. Generation of recombinant baculovirus via liposome-mediated transfection. Biotechniques 11:310–312 (1991).
Höpfl, R., et al. Skin test for HPV type 16 proteins in cervical intraepithelial . . . Lancet 337:373–374 (1991).
Jarrett, W., et al. Studies on vaccination against papillomaviruses . . . Veterinary Record 126:449–452 (1990).
Jarrett, W., et al. Studies on vaccination against papillomaviruses . . . Virology 184:33–42 (1991).
Jenison, S., et al. Evidence of prevalent genital-type human papillomavirus infections . . . J. Infectious Dis. 162:60–69 (1990).
Jenson, A., et al. Identification of linear epitopes of the BPV-1 L1 protein . . . Pathobiology 59:396–403 (1991).
Jin, X., et al. Identification of L2 open reading frame gene products of bovine . . . J. Gen. Virology 70:1133–1140 (1989).
Kajigaya, S., et al. Self-assembled B19 parvovirus capsids, produced in a baculovirus . . . Proc. Natl. Acad. Sci. USA 88:4646–4650 (1991).
Larsen, P., et al. Proteins present in bovine papillomavirus particles. virology 61:3596–3601 (1987).
Liddington, R., et al. Structure of simian virus 40 at 3.8-A resolution. Nature 354:278–284 (1991).
Lin, YI, et al. Effective vaccination against papilloma development by immunization . . . Virology 187:612–619 (1992).
McLean, C., et al. Production and characterization of a monoclonal antibody . . . J. Clin. Pathol. 43:488–492 (1990).

(List continued on next page.)

Primary Examiner—Mary E. Mosher
Attorney, Agent, or Firm—Knobbe, Martens, Olson & Bear, LLP

[57] ABSTRACT

Recombinant papillomavirus capsid proteins that are capable of self-assembly into capsomer structures and viral capsids that comprise conformational antigenic epitopes are provided. The capsomer structures and viral capsids, consisting of the capsid proteins that are expression products of a bovine, monkey or human papillomavirus L1 conformational coding sequence proteins, can be prepared as vaccines to induce a high-titer neutralizing antibody response in vertebrate animals. The self assembling capsid proteins can also be used as elements of diagnostic immunoassay procedures for papillomavirus infection.

12 Claims, 3 Drawing Sheets

OTHER PUBLICATIONS

Nakai, Y., et al. Monoclonal antibodies to genus– and type–specific papillomavirus . . . Intervirol. 25:30–37 (1986).

Olson, C., et al. Further observations on immunity to bovine cutaneous papillomatosis. Amer. J. Vet. Res. 21:233–242 (1960).

Pilacinski, W., et al. Immunization against bovine papillomavirus infection. Biotechnology 2:136–156 (1984).

Saiki, R.K. et al. Primer–directed enzymatic amplification of DNA with a thermostable . . . Science 239:487–491 (1987).

Schiffman, M., et al. Recent progress in defining the epidemiology of human papillomavirus . . . National Cancer Inst. 84:394–398 (1992).

Seedorf, K., et al. Human papillomavirus type 16 DNA sequence. Virology 145:181–185 (1985).

Stevens, C., et al. Yeast–recombinant hepatitis B vaccine. JAMA 257:2612–2616 (1987).

Stites, D. et al. Clinical laboratory methods of detecting cellular immune function . . . Basic and Clinical Immunology 3:382–397 (1980).

Summers, D., et al. A manual of methods of baculovirus vectors and insect cell culture . . . Bulletin No. 1555, Texas A & M University, 1988.

Zhou, J. et al. Expression of vaccinia recombinant HPV 16 L1 and L2 ORF proteins in epithelial cells . . . J. Virology 185:251–257 (1991).

Zur Hausen, H. Viruses in human cancers. Science 254:1167–1173 (1991).

Wang, X., et al. Baculovirus vectors for multiple gene expression and for occluded . . . Gene 100:131–137 (1991).

Browne, H.M., et al.Analysis of the L1 gene product of human papillomavirus type 16 by . . . J. Gen. Virol. 69:1263–1273 (1988).

Davies, D.H., et al. Definition of murine T helper cell determinants in the major capsid . . . J. Gen. Virol. 71:2691–2698 (1990).

Jenkins, O., et al. An antigen chimera of poliovirus induces antibodies against . . . J. of Virology 1201–1206 (1990).

Montross, L., et al. Nuclear assembly of polyomavirus capsids in insect cells . . . J. of Virology 4991–4998 (1991).

Zhou, J., et al. The induction of cytotoxic T–Lymphocyte precursor cells by recombinant . . . Virology 181:203–210 (1991).

Zhou, J., et al. Increased antibody responses to human papillomavirus type 16 L1 protein . . . J. of Gen Virology 71:2185–2190 (1990).

Zhou, J., et al. Identification of the nuclear localization signal of human papillomavirus . . . Virology 185:626–632 (1991).

Kirnbauer, R., et al., Efficient self–assembly of human papillomavirus type 16L1 and L1–L2 . . . Journal of Virology, 67:6929–6936 (1993).

Xi, et al., Baculovirus expression of the human papillomavirus type 16 capsid proteins . . . Journal of General Virology, 72:2981–2988 (1991).

Watson, J.D., et al., Eds, 1983, Recombinant DNA—A Short Course, W.J. Freeman and Company (New York) publishers, p. 236.

Carter, J.J., et al., 1991, Expression of Human Papillomavirus Proteins in Yeast . . . , Virology 182:513–521.

Zhou, J., et al., 1992, Definition of Linear Antigenic Regions of the HPV16 L1 Capsid Protein . . . , Virology 189:592–599.

Rose, R.C., et al., 1990, Expression of the Full Length Products of the Human Papillomavirus Type . . . , J. Gen. Virology 71:2725–2729.

Steele, J.C., et al., 1990, Humoral assays of human sera to disrupted and nondisrupted epitopes . . . , Virology 174:388–398.

Cason, J., et al., 1992, Detection of antibodies to a linear epitope on the major coat protein . . . , Int. J. Cancer 50:349–355.

Beiss, B., et al., 1991, Virology, 184:460–464.

Lehtinen, M., et al., 1990, Biochemical and Biophysical Research Communications 172:1378–1383.

Yaegashi, N., et al., 1991, J. Virology, 65:1578–1583.

Ghim, S.–J., et al., 1992, PHV–1 L1 protein expressed in cos cells displays conformational epitopes . . . , Virology 190:548–552.

"Immunotherapeutic products will have $2.4 billion European market in 1995", 1992, Biotechnology News 12(8):2.

Kirnbauer, R., et al., 1994, A virus–like particle enzyme–linked immunosorbent assay . . . , J. Nat. Cancer Inst. 86:494–499.

Galloway, D.A., [Editorial], 1994, Papillomavirus capsids: a new approach to identify . . . , J. Nat. Cancer Inst. 86:474–475.

"In this issue," 1994, J. Nat. Cancer Inst. 86:47.

Roden, R.B.S., et al., 1994, Interactions of papillomavirus with the cell surface, J. Virology 68:7260–7266.

Kirnbauer, R. et al., 1992, Papillomavirus L1 major capsid protein self–assembles into virus . . . Proc. Natl. Acad. Sci. 89:12180–12184.

Hagansee, M.E., et al., 1993, Self–assembly of human papillomavirus type 1 capsids by expression . . . , J. Virology 67:315–322.

Rose, R.C., et al., 1993, Expression of human papillomavirus type 11 L1 protein in insect cells . . . , J. Virology 67:1936–1944.

Howley, P.M., In: Fundamental Virology, Second Edition, Fields, B.N., et al., Editors, Raven Press, 1991, pp. 743–768.

Bernard, J.–U., et al., In: Human Pathogenic Papillomaviruses/Current Topics in Microbiology & Immunology, vol. 186, zur Hausen, H., Editor, Springer–Verlag, pp. 34–54, 1994.

Sasagawa, T., et al., 1994, Synthesis and assembly of virus–like particles of the human type 6 and 16 in fission yeast . . . Programme & Abstract Book, 13th Intl. Papillomavirus Conf., Amsterdam, p. 316.

Kirnbauer, R., et al., 1994, A vaccine of virus–like particles made in insect cells can inhibit papillomavirus infection . . . , Programme & Abstract Book, 13th Intl. Papillomaviruses Conf., Amsterdam, p. 154.

Ghim, S.–J., et al., 1994, Papilloma extracts and recombinant L1 protein protect completely against papillomavirus . . . , Programme & Abstract Book, 13th Intl. Papillomavirus Conf., Amsterdam, p. 56.

Charval, B., et al., Serum antibodies to papillomavirus–like particles type 6, 11 and 16 in patients . . . , Programme & Abstract Book, 13th Intl. Papillomavirus Conf., Amsterdam, p. 316, 1994.

Rose, R., et al., 1994, Seroresponses of patients with HPV –6 –16 –18 o r–31 infections to recombinant . . . , Programme & Abstract Book, 13th Intl. Papillomavirus Conf., Amsterdam p. 327.

Rose, R., et al., 1994, Antigenic cross reactivity between HPV6 and HPV11, Programme & Abstract Book, 13th Intl. Papillomavirus Conf., Amsterdam p. 328.

Cheng, G., et al., 1994, Sero–reactivity of women to virus–like particles made with a Zaire strain of HPV16 . . . , Abstract presented at the NIH Summer Student Poster Day Session.

Kirnbauer, R., et al., 1993, IN: Vaccines '93, Ginsberg, H.S. et al., Editor, Cold Spring Harbor Laboratory Press, pp. 305–310.

Campo, M.S., et al., 1993, Prophylactic and therapeutic vaccination against mucosal papillomavirus, J. Gen. Virology 74:945–953.

SELF-ASSEMBLING RECOMBINANT PAPILLOMAVIRUS CAPSID PROTEINS

This application is a divisional of U.S. patent application Ser. No. 08/032,869, filed Mar. 16, 1993, now U.S. Pat. No. 5,437,951 which is a continuation in part of Ser. No. 07/941,371, filed Sep. 3, 1992.

That application is hereby incorporated by reference as if fully set forth herein. The invention relates to recombinant viral proteins. It relates particularly to recombinant viral proteins that are suitable for use in the diagnosis, prophylaxis and therapy of vital infections.

Papillomaviruses infect the epithelia of a wide variety of species of animals, including humans, generally inducing benign epithelial and fibro-epithelial tumors, or warts, at the site of infection. Each species of vertebrate is infected by a distinct group of papillomaviruses, each papillomavirus group comprising several papillomavirus types. For example, more than 60 different human papillomavirus (HPV) genotypes have been isolated. Papillomaviruses are highly species specific infective agents; for example, a bovine papillomavirus cannot induce papillomas in a heterologous species, such as humans. Papillomavirus types ALSO appear to be highly specific as immunogens in that a neutralizing immunity to infection against one papillomavirus type does not usually confer immunity against another type, even when the types infect an homologous species.

In humans, genital warts, which are caused by human papillomaviruses, represent a sexually transmitted disease. Genital warts are very common, and subclinical, or inapparent HPV infection is even more common than clinical infection. Some benign lesions in humans, particularly those arising from certain papillomavirus types, undergo malignant progression. For that reason, infection by one of the malignancy associated papilloma virus types is considered one of the most significant risk factors in the development of cervical cancer, the second most common cancer of women worldwide (zur Hausen, H., 1991; Schiffman, M. 1992). Several different HPV genotypes have been found in cervical cancer, with HPV16 being the most common type that is isolated from 50% of cervical cancers.

Immunological studies demonstrating the production of neutralizing antibodies to papillomavirus antigens indicate that papillomavirus infections and malignancies associated with these infections in vertebrate animals could be prevented through immunization; however the development of effective papillomavirus vaccines has been impeded by a number of difficulties.

First, it has not been possible to generate in vitro the large stocks of infectious virus required to determine the structural and immunogenic features of papillomavirus that are fundamental to the development of effective vaccines. Cultured cells express papillomavirus oncoproteins and other non-structural proteins and these have been extensively studied in vitro; but expression of the structural viral proteins, L1 and L2 (and the subsequent assembly of infectious virus) occurs only in terminally differentiated layers of infected epithelial tissues. Therefore, the characterization of viral genes, proteins, and structure has necessarily been assembled from studies of virus harvested from papillomas. In particular, papillomavirus structure and related immunity have been carried out in the bovine papillomavirus system because large amounts of infectious virus particles can be isolated from bovine papillomavirus (BPV) warts.

The information derived from studies of papillomavirus structure to date indicates that all papillomaviruses are non-enveloped 50–60 nmicosahedral structures (Crawford, L., et al., 1963) which are comprised of conserved L1 major capsid protein and less well conserved L2 minor capsid protein (Baker, C., 1987). There is no sequence relationship between the two proteins. The function and location of L2 in the capsid is unclear; however immunologic data suggests that most of L2 is internal to L1.

Recently, high resolution cryoelectron microscopic analysis of BPV1 and HPV1 virions has determined that the two viruses have a very similar structure, with 72 pentameric capsomers, each capsomer presumably composed of five L1 molecules, forming a virion shell with T=7 symmetry (Baker, T., 1991). The location of the minor L2 capsid protein in the virion has not been determined, and it is not certain whether L2 or other viral proteins are needed for capsid assembly. Superficially, papillomavirus structure resembles that of the polyoma 45 nm virion, which has the same symmetry and capsomere number (Liddington, R., et al., 1991); however, the systems of intracapsomer contact for polyomavirus and papillomavirus species are different, and the major and minor capsid proteins of polyomavirus are not genetically related to L1 and L2.

Bovine papillomavirus studies are facilitated by a quantitative focal transformation infectivity assay developed for BPV that is not available for HPV (Dvoretzky, I., et al., 1980), and an understanding of immunity to papillomavirus has therefore also been derived from the bovine papillomavirus system. Limited studies using intact bovine papillomavirus demonstrated that the non-cutaneous inoculation of infectious or formalin-inactivated BPV virus was effective as a vaccine to prevent experimental BPV infection in calves (Olson, C., et al., 1960; Jarrett, W., et al., 1990). Unfortunately, BPV virions cannot be used to develop vaccines against papillomavirus which infects other species, or even vaccines against other bovine types, because of the great specificity of these viruses, as well as concern for the oncogenic potential of intact viral particles.

A significant conclusion of studies of papillomavirus immunity is that the ability of antibodies to neutralize papilloma virus appears to be related to their ability to react with type-specific, conformationally dependent epitopes on the virion surface. For example, rabbit antisera raised against infectious BPV1 virions inhibits focal transformation of C127 cells (Doretzky, I., et al., 1980), as well as the transformation of fetal bovine skin grafts; whereas antisera raised against denatured virions does not (Ghim, S., et al., 1991).

In contrast, neutralizing sera generated against bacterially derived BPV L1 and L2 (Pilacinski, W. et al., 1984; Jin, X., et al., 1989) and against in vitro synthesized cottontail rabbit papillomavirus (CRPV) L1 and L2 (Christensen, N., et al., 1991; Lin, Y-L, et al., 1992), neither of which has the structural features of native virions, had low titers, and the use of recombinant HPV L1 fusion peptides expressed in *E. coli* to detect cellular immune reactivity has had only limited success (Höpfl, R. et al., 1991). The results in the BPV system are consistent with those of the HPV system, in which monoclonal antibodies that neutralized HPV11 infection in a mouse xenograft assay recognized native, but not denatured, HPV11 virions (Christensen, N., et al., 1990).

There have been isolated attempts to produce papillomavirus capsids in vitro. Zhou, J. et al. (1991) and (1992) produced virus-like particles by cloning HPV L1 and L2 genes, and HPV L1 and L2 genes in combination with HPV E3/E4 genes into a vaccinia virus vector and infecting CV-1 mammalian cells with the recombinant vaccinia virus. These studies were interpreted by Zhou to establish that expression of HPV16 L1 and L2 proteins in epithelial cells is necessary and sufficient to allow assembly of virion type particles. Cells infected with doubly recombinant vaccinia virus which expressed L1 and L2 proteins showed small (40 nm ) virus-like particles in the nucleus that appeared to be incompletely assembled arrays of HPV capsomers. Expressing L1 protein alone, or L2 protein alone, was expressed did not produce virus-like particles; cells doubly infected with singly recombinant vaccinia virus containing L1 and L2 genes also did not produce particles. No neutralizing activity was reported.

Ghim et al., (1992) reported that when L1 from HPV1, a non-genital virus type associated mainly with warts on the hands and feet, was expressed in mammalian cells, the L1 protein contained conformational epitopes found on intact virions. Ghim did not determine if particles were produced, nor was it evaluated if the L1 protein might induce neutralizing antibodies. Even more recently, Hagansee, et al. (1993) reported that when L1 from HPV1 was expressed in human cells, it self-assembled into virus-like particles. No neutralizing antibody studies were performed.

Studies in other virus systems, for example, parvovirus, indicate that capsid assembly alone may not confer immunogenicity. Parvovirus VP2, by itself, was able to self-assemble when expressed in insect cells, but only particles containing both VP1 and VP2 were able to induce neutralizing antibodies (Kajigaya, S., et al., 1991).

It would be advantageous to develop methods for producing renewable papillomavirus reagents of any selected species and type in cell culture. It would also be beneficial to produce such papillomavirus reagents having the immunity conferring properties of the conformed native virus particles that could be used as a subunit vaccine.

It is therefore the object of the invention to provide these recombinant conformed papillomavirus proteins, as well as methods for their production and use.

SUMMARY OF THE INVENTION

The invention is directed to the diagnosis and prevention of papillomavirus infections and their benign and malignant sequelae by providing recombinant papillomavirus capsid proteins that self assemble to form capsomer structures comprising conformational epitopes that are highly specific and highly immunogenic. Therefore, according to the invention there is provided a genetic construct, comprising a papillomavirus L1 conformational coding sequence, inserted into a baculovirus transfer vector, and operatively expressed by a promoter of that vector. The papillomavirus L1 conformational coding sequence can be isolated from a bovine, monkey, or human gene. In a preferred embodiment, the papillomavirus L1 conformational coding sequence is isolated from a wild type HPV16 gene. In a particularly preferred embodiment, the papillomavirus L1 conformational coding sequence is Sequence ID No. 2. The genetic construct can further comprise a papillomavirus L2 coding sequence.

According to another aspect of the invention there is provided a non-mammalian eukaryotic host cell transformed by the genetic constructs of the invention.

According to yet another aspect of the invention there is provided a method for producing a recombinant papillomavirus capsid protein, assembled into a capsomer structure or a portion thereof, comprising the steps of (1) cloning a papillomavirus gene that codes for an L1 conformational capsid protein into a transfer vector wherein the open reading frame of said gene is under the control of the promoter of said vector; (2) transferring the recombinant vector into a host cell, wherein the cloned papillomavirus gene expresses the papillomavirus capsid protein; and (3) isolating capsomer structures, comprising the papillomavirus capsid protein, from the host cell. In a preferred embodiment, the cloned papillomavirus gene consists essentially of the conformational L1 coding sequence, and the expressed protein assembles into capsomer structures consisting essentially of L1 capsid protein. In another preferred embodiment, the cloning step of the method further comprises the cloning of a papillomavirus gene coding for L2 capsid protein, whereby said L1 and L2 proteins are coexpressed in the host cell, and wherein the isolated capsomer structures comprise L1 and L2 capsid proteins; provided that said transfer vector is not a vaccinia virus when said host cell is a mammalian cell. The conformational L1 coding sequence can be cloned from a bovine, monkey, or human papillomavirus. According to a preferred embodiment, the conformational L1 coding sequence is cloned from a wild type HPV16 papillomavirus. In a particularly preferred embodiment, the conformational L1 coding sequence is Sequence ID N. 2. Also in a preferred embodiment, the host cell into which the genetic construct is transfected is an insect cell. Also preferred are embodiments wherein the transfer vector is a baculovirus based transfer vector, and the papillomavirus gene is under the control of a promoter that is active in insect cells. Accordingly in this embodiment, the recombinant baculovirus DNA is transfected into Sf-9 insect cells, preferably co-transfected with wild-type baculovirus DNA into Sf-9 insect cells.

In an alternative embodiment of the method of the invention, the transfer vector is a yeast transfer vector, and the recombinant vector is transfected into yeast cells. According to yet another aspect of the invention there is provided a virus capsomer structure, or a portion thereof, consisting essentially of papillomavirus L1 capsid protein, produced by the method the invention. Alternatively, the virus capsomer structure can consist essentially of papillomavirus L1 and L2 capsid proteins, produced by the method of the invention. In a particularly preferred embodiment, the virus capsomer structure comprises papillomavirus L1 capsid protein that is the expression product of an HPV16 L1 DNA cloned from a wild type virus. The virus capsids or capsomer structures of the invention, or portions or fragments thereof, can consist essentially of papillomavirus L1 capsid protein. Alternatively, these capsids or capsomer structures or their fragments can consist essentially of wild type HPV16 papillomavirus L1 capsid protein.

The virus capsid structures according to any of the methods of the invention comprise capsid proteins having immunogenic conformational epitopes capable of inducing neutralizing antibodies against native papillomavirus. The capsid proteins can be bovine, monkey or human papillomavirus L1 proteins. In a preferred embodiment, the papillomavirus L1 capsid protein is the expression product of a wild type HPV16 L1 gene. In a particularly preferred embodiment, the HPV16 L1 gene comprises the sequence of Sequence ID No. 2.

According to yet another aspect of the invention there is provided a unit dose of a vaccine, comprising a peptide having conformational epitopes of a papillomavirus L1 capsid protein, or L1 protein and L2 capsid proteins, in an effective immunogenic concentration sufficient to induce a papillomavirus neutralizing antibody titer of at least about $10^3$ when administered according to an immunizing dosage schedule. In a preferred embodiment, the vaccine comprises an L1 capsid protein which is an HPV16 capsid protein. In a particularly preferred embodiment, the vaccine comprises an L1 capsid protein that is a wild type HPV16 L1 protein.

Use of the L1 open reading frame (ORF) from a wild type HPV16 papillomavirus genome, according to the methods of the invention, particularly facilitates the production of preparative amounts of virus-like particles on a scale suitable for vaccine use.

According to yet another aspect of the invention, there is provided a method of preventing or treating papillomavirus infection in a vertebrate, comprising the administration of a papillomavirus capsomer structure or a fragment thereof according to the invention to a vertebrate, according to an immunity-producing regimen. In a preferred embodiment, the papillomavirus capsomer structure comprises wild type HPV16 L1 capsid protein.

The invention further provides a method of preventing or treating papillomavirus infection in a vertebrate, comprising the administration of the papillomavirus capsomer structure of the invention, or a vaccine product comprising the capsomer structure to a vertebrate, according to an immunity-producing regimen. In a preferred embodiment, the papillomavirus vaccine comprises wild type HPV16 L1 capsid protein.

Also within the scope of the invention is a method for immunizing a vertebrate against papillomavirus infection, comprising administering to the vertebrate a recombinant genetic construct of the invention comprising a conformational papillomavirus L1 coding sequence, and allowing said coding sequence to be expressed in the cells or tissues of said vertebrate, whereby an effective, neutralizing, immune response to papillomavirus is induced. In a preferred embodiment, the conformational papillomavirus L1 coding sequence is derived from human papillomavirus HPV16. In a particularly preferred embodiment, the human papillomavirus HPV16 is a wild type papillomavirus.

According to yet another aspect of the invention, there is provided a method of detecting humoral immunity to papillomavirus infection in a vertebrate comprising the steps of: (a) providing an effective antibody-detecting amount of a papillomavirus capsid peptide having at least one conformational epitope of a papillomavirus capsomer structure; (b) contacting the peptide of step (a) with a sample of bodily fluid from a vertebrate to be examined for papillomavirus infection, and allowing papillomavirus antibodies contained in said sample to bind thereto, forming antigen-antibody complexes; (c) separating said complexes from unbound substances; (d) contacting the complexes of step (c) with a detectably labelled immunoglobulin-binding agent; and (e) detecting anti-papillomavirus antibodies in said sample by means of the labelled immunoglobulin-binding agent that binds to said complexes. In a preferred embodiment of this aspect of the invention, the peptide consists essentially of papillomavirus L1 capsid protein. According to an alternative embodiment, the peptide consists essentially of the expression product of a human papillomavirus HPV16. In a particularly preferred embodiment, the peptide consists essentially of the expression product of a wild type human papillomavirus HPV16 gene, for example, the peptide can consist essentially of the expression product of Sequence ID No. 2.

According to yet another aspect of the invention, there is provided a method of detecting papillomavirus in a specimen from an animal suspected of being infected with said virus, comprising contacting the specimen with antibodies having a specificity to one or more conformational epitopes of the capsid of said papillomavirus, wherein the antibodies have a detectable signal producing label, or are attached to a detectably labelled reagent; allowing the antibodies to bind to the papillomavirus; and determining the presence of papillomavirus present in the specimen by means of the detectable label.

According to yet another aspect of the invention, there is provided a method of determining a cellular immune response to papillomavirus in an animal suspected of being infected with the virus, comprising contacting immunocompetent cells of said animal with a recombinant wild type papillomavirus L1 capsid protein, or combined recombinant L1 and L2 capsid proteins according to the invention; and assessing cellular immunity to papillomavirus by means of the proliferative response of said cells to the capsid protein. In a preferred embodiment of this aspect of the invention, the recombinant papillomavirus protein is introduced into the skin of the animal.

According to yet another aspect of the invention there is provided a papillomavirus infection diagnostic kit, comprising capsomer structures consisting essentially of papillomavirus L1 capsid protein, or capsomer structures comprising papillomavirus L1 protein and L2 capsid proteins, or antibodies to either of these capsomer structures, singly or in combination, together with materials for carrying out an assay for humoral or cellular immunity against papillomavirus, in a unit package container.

DETAILED DESCRIPTION OF THE INVENTION

Figure 1:
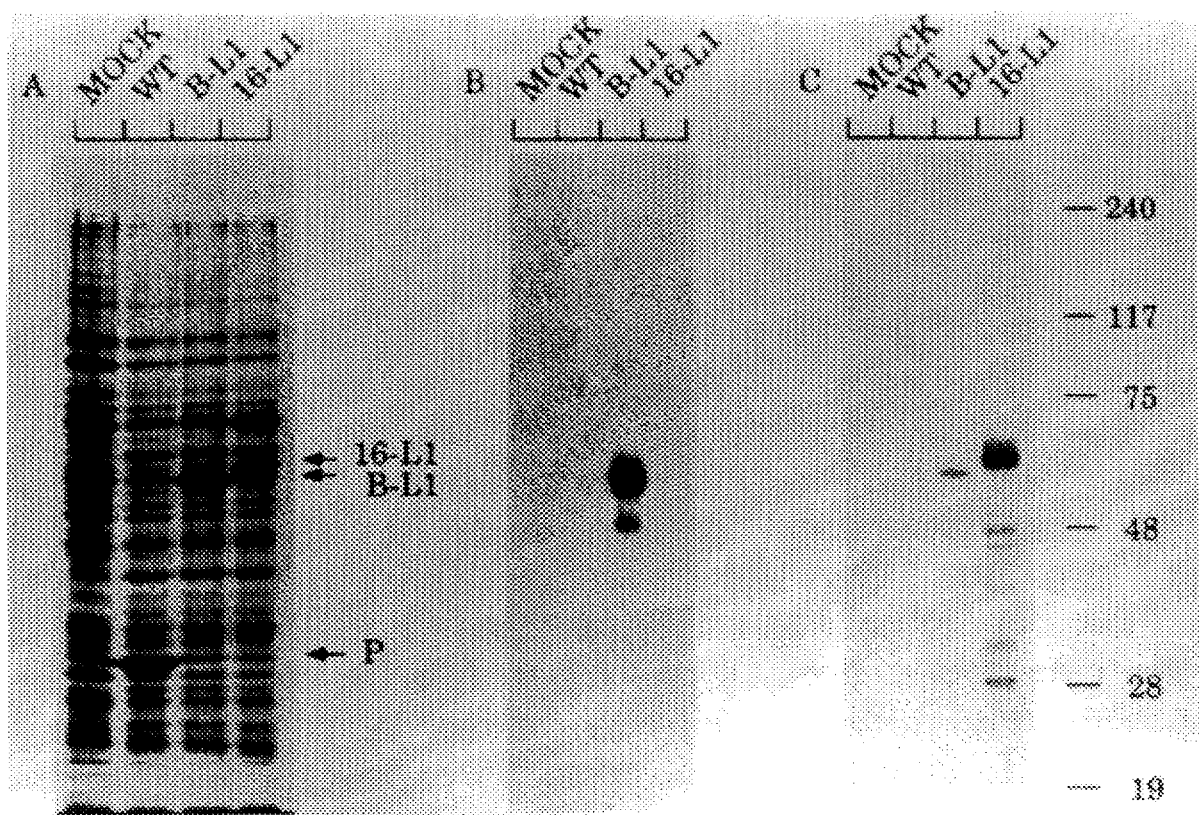
FIG. 1 shows the expression of BPV L1 and HPV16 L1 by means of recombinant virus as demonstrated by SDS-PAGE analysis of lysates from infected insect cells.

We have discovered that the gene coding for the L1 major capsid protein of BPV or HPV16, following introduction into host cells by means of an appropriate transfer vector, can express L1 at high levels, and that the recombinant L1 has the intrinsic capacity to self-assemble into empty capsomer structures that closely resemble those of an intact virion.

Further, the self-assembled recombinant L1 capsid protein of the invention, in contrast to L1 protein extracted from recombinant bacteria, or denatured virions, has the efficacy of intact papillomavirus particles in the ability to induce high levels of neutralizing antiserum that can protect against papillomavirus infection. The high level of immunogenicity of the capsid proteins of the invention implies strong antibody binding properties that make them sensitive agents in serological screening tests to detect and measure antibodies to conformational virion epitopes. Their immunogenicity also indicates that the capsid proteins of the invention can also be used as highly effective vaccines or immunogens to elicit neutralizing antibodies to protect a host animal against infection by papillomavirus. These observations were recently published in Kirnbauer, et al., (1992), and formed the basis of U.S. application Ser. No. 07/941,371.

We have now discovered that the capsid protein L1 expressed by wild type HPV16 genomes isolated from benign papillomavirus lesions, when expressed in the baculovirus system described, will self-assemble with an efficiency heretofore unknown and comparable to that of bovine papillovirus L1 capsid protein.

The HPV16 L1 Gene Sequences

The source of HPV16 L1 DNA, as disclosed in published studies, for example, by Zhou, et al.(1991) was the prototype clone, GenBankAccession No. K02718, that had been isolated from a cervical carcinoma (Seedoff, et al., 1985). We have found that L1 from wild type HPV16 genome, which differs from the prototype genome by a single point mutation, will self-assemble into virus-like particles with an efficiency similar to that seen with BPV L1 or BPV L1/L2. Compared with the self-assembly seen when L1 from the prototype HPV genome is used with L2, L1 from a wild-type genome self-assembles at least 100 times more efficiently.

To provide genetic insight into the self-assembly efficiency of different HPV16 L1 expression products, the open reading frames from HPV16 L1 genes isolated from both benign lesions and lesions associated with dysplasia or carcinoma were sequenced.

The analysis detected two errors in the published sequence of the published L1 sequence of the prototype strain, as follows:

(1) there should be an insertion of three nucleotides (ATC) between nt 6902 and 6903, which results in the insertion of a serine in the L1 protein; and (2) there should be a deletion in the published prototype sequence of three nucleotides (GAT), consisting of nt 6952–6954, which deletes an aspartate from the L1 protein sequence. The corrected nucleotide sequence of the prototype HPV16 L1 genome, consisting of nt 5637–7155, is that of Sequence ID No. 1, listed herein.

The numbering of the nucleotide bases in Sequence ID Nos. 1 and 2 is indexed to 1, and the numbering of nucleotide bases of the published HPV sequence, that is from nt 5638–7156, corresponds to those of the sequence listing from 1–1518. The sites referred to in the original sequence can be thus readily identified by one skilled in the art.

Three other HPV16 L1 genomes, clone 16PAT; and clones 114/16/2 and 114/16/11, were sequenced and those sequences compared to that of the corrected prototype.

Clone 16PAT, kindly provided by Dennis McCance at the University of Rochester School of Medicine, and cloned from a dysplastic (pre-malignant) lesion of the cervix, expresses an L1 that does not self-assemble efficiently.

Clones 114/16/2 and 114/16/11, kindly provided by Matthias Dürst of the German Cancer Research Center in Heidelburg, were both cloned from non-malignant lesions, and both expressed L1 protein that self-assembled efficiently.

Comparison of Genetic Characteristics of HPV16 L1 associated with Dysplasia, Malignant Progression and Benign Lesions Clone 16PAT, isolated from papillomavirus infected dysplastic lesions and the prototype HPV16, isolated from malignant cervical carcinoma, both encode Histidine at nt 6242–6244, while clones 2 and 11, isolated from benign papillomavirus infected lesions (like isolates of many other papillomavirus) encode Aspartate at this site.

It appears that this single amino acid difference between the prototype, malignancy-associated HPV16 species, and the HPV16 species from benign lesions accounts for the difference in self-assembly efficiency. It is likely that among closely related HPV types, Aspartate at this locus may be necessary for efficient self-assembly, and that the substitution of Histidine for Aspartate impairs this ability in the capsid protein. The impairment in capsid assembly in malignancy-associated viruses, associated with loss of the conformational epitopes required for the production of neutralizing antibodies, may also be linked to a lowered immunogenicity which would allow the papillomavirus to escape immune control.

Accordingly, HPV16 L1 genes that express capsid protein that self-assembles efficiently can be obtained by (1) isolation of the wild type HPV16 L1 open reading frame from benign lesions of papillomavirus infection; or (2) carrying out a site specific mutation in the prototype sequence at nt 6242–6244 to encode Aspartate.

Recombinant Capsid Protein

The method of the invention provides a means of preparing recombinant capsid particles for any papillomavirus. Particles consisting of either L1 or L2 capsid protein alone, or consisting of both L1 and L2 capsid proteins together can be prepared. L1/L2 capsid protein particles are more closely related to the composition of native papillomavirus virions, but L2 does not appear to be as significant as L1 in conferring immunity, probably because most of L2 is internal to L1 in the capsid structure. Although L1 can self-assemble by itself, in the absence of L2, self-assembled L1/L2 capsid protein particles are more closely related to the composition of native papillomavirus virions. Accordingly, particles comprising L1 alone are simpler, while those comprising L1/L2 may have an even more authentic structure. Both self-assembled L1 and L1/L2 particles induce high-titer neutralizing antibodies and may therefore be suitable for vaccine production. Particles comprising L1 capsid protein expressed by a wild type HPV genome, either as L1 alone or L1/L2 together, are particularly preferred.

Production of the recombinant L1, or combined L1/L2, capsid particles is carried out by cloning the L1 (or L1 and L2) gene(s) into a suitable vector and expressing the corresponding conformational coding sequences for these proteins in a eukaryotic cell transformed by the vector. It is believed that the ability to form a capsid-like structure is intimately related to the ability of the capsid protein to generate high-titer neutralizing antibody, and that in order to produce a capsid protein that is capable of self-assembling into capsid structures having conformational epitopes, substantially all of the capsid protein coding sequence must be expressed. Accordingly, substantially all of the capsid protein coding sequence is cloned. The gene is preferably expressed in a eukaryotic cell system. Insect cells are preferred host cells; however, yeast cells are also suitable as host cells if appropriate yeast expression vectors are used. Mammalian cells similarly transfected using appropriate mammalian expression vectors can also be used to produce assembled capsid protein, however, cultured mammalian cells are less advantageous because they are more likely than non-mammalian cells to harbor occult viruses which might be infectious for mammals.

According to a preferred protocol, a baculovirus system is used. The gene to be cloned, substantially all of the coding sequence for bovine papillomavirus (BPV1) or human papillomavirus (HPV16) L1 capsid protein, or human papillomavirus HPV16 L1 and L2, is inserted into a baculovirus transfer vector containing flanking baculovirus sequences to form a gene construct, and the recombinant DNA is co-transfected with wild type baculovirus DNA into Sf-9 insect cells as described in Example 1, to generate recombinant virus which, on infection, can express the inserted gene at high levels. The actual production of protein is made by infecting fresh insect cells with the recombinant baculovirus; accordingly, the L1 capsid protein and the L1 and L2 capsid proteins are expressed in insect cells that have been infected with recombinant baculovirus as described in Example 2.

In the procedure of Example 1, the complete L1 gene of BPV1 was amplified by polymerase chain reaction (PCR; Saiki, R., et al., 1987) and cloned into AcMNPV (Autographa californica nuclear polyhedrosis virus) based baculovirus vector (Summers, M. et al., 1987). The L1 open reading frame was put under the control of the baculovirus polyhedrin promoter. After co-transfection of the L1 clone with the wild type (wt) baculovirus DNA into Sf-9 insect cells (ATCC Accession No. CRL1711) and plaque purification of recombinant clones, high titer recombinant virus was generated. Extracts from cells infected with wt AcMNPV or BPV1 L1 recombinant viruses (AcBPV-L1) (Example 2) were analyzed by polyacrylamide gel electrophoresis. After Coomassie blue staining, a unique protein of the predicted size, 55 kilodaltons, was detected in extracts from the cultures infected with the AcBPV1-L1 virus (FIG. 1A). The identity of this protein as BPV L1 was verified by immunoblotting (FIG. 1B), using a BPV L1 specific monoclonal antibody (Nakai, Y., et al., 1986).

To test the hypothesis that papillomavirus L1 has the ability to self-assemble into virus-like particles when overexpressed in heterologous cells, electron micrographs of thin sections from AcBPV-L1 infected cells were examined for the presence of papillomavirus-like structures. Cells infected with the BPV recombinant virus contained many circular structures of approximately 50 nm which were preferentially localized in the nucleus; these structures were absent from wild type baculovirus infected cells. These results suggested that self assembly of L1 into virus-like particles had occurred, since in vivo papillomavirus virion assembly takes place in the nucleus and the diameter of the virions has been reported as 55 nm.

Figure 2:
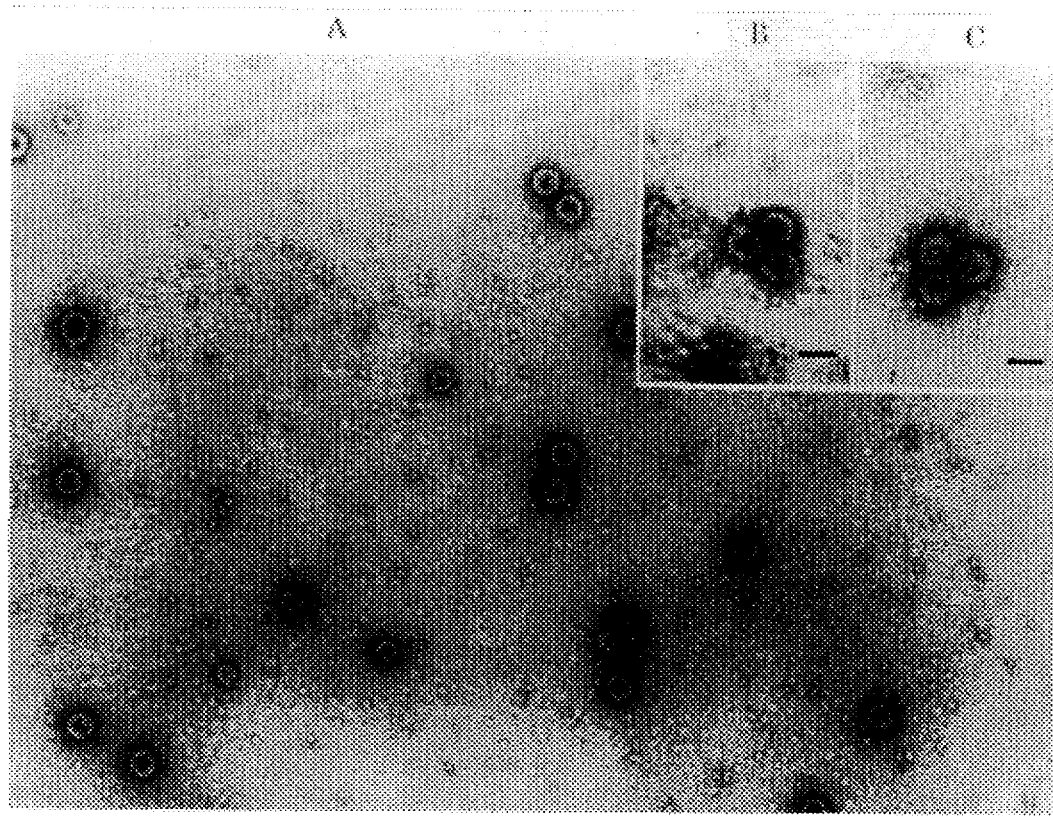
FIG. 2 shows the conformation of purified recombinant BPV L1 and HPV16 L1 capsid proteins as demonstrated by electron microscopy, compared with authentic BPV virions.

Following expression of the conformed capsid protein in the host cell, virus particles are purified from lysates of infected cells as described in Example 4. To obtain further evidence that the L1 protein had self-assembled, virus-like particles were isolated from the infected insect cells by means of gradient centrifugation (FIG. 2).

High molecular mass structures were separated from lysates of L1 recombinant or wild type infected cells by centrifugation through a 40% sucrose cushion and the pelleted material was subjected to CsCl density gradient centrifugation. Fractions were collected and tested for reactivity to the BPV L1 specific monoclonal antibody by immunoblotting.

L1 positive fractions from the gradient were adsorbed onto carbon film grids, stained with 1% uranyl acetate and examined by transmission electron microscopy. The positive fractions contained numerous circular structures that exhibited a regular array of capsomers (FIG. 2A). Consistent with previous reports of the density of empty BPV virions (Larsen, P., et al., 1987), the density of the CsCl fraction containing the peak of the virus-like particles was approximately 1.30 gm/ml. Most were approximately 50 nm in diameter, although smaller circles and partially assembled structures were also seen. The larger particles were very similar in size and subunit structure to infectious BPV virions that had been stained and photographed concurrently (FIG. 2B). These particles were not observed in preparations from mock infected or wt AcMNPV infected cells. These results indicate that BPV L1 has the intrinsic capacity to assemble into virus-like particles in the absence of L2 or other papillomavirus proteins. In addition, specific factors limited to differentiating epithelia or mammalian cells are not required for papillomavirus capsid assembly.

To determine if the ability to self-assemble in insect cells is a general feature of papillomavirus L1, we also expressed the L1 of HPV16, the HPV type most often detected in human genital cancers, via an analogous recombinant baculovirus. A protein of the expected 58 kd size was expressed at high levels in the insect cells infected with the HPV16-L1 recombinant virus (FIG. 1A) and it reacted strongly with an HPV16 L1 monoclonal antibody (which also reacted weakly with BPV L1; FIG. 1C). After CsCl gradient purification, immunoreactive fractions were examined by electron microscopy and found to contain 50 nm papillomavirus-like particles (FIG. 2C). Although somewhat fewer completely assembled particles were seen in the human system in comparison to the BPV L1 preparations, possibly due to the lower levels of expression or greater extent of HPV16 L1 degradation (FIG. 1), the results conclusively indicate that the L1 of the HPV16 and presumably the L1 proteins of other types, have the intrinsic capacity to assemble into virion-type structures. Preparations of recombinant papillomavirus capsid particles for Rhesus monkey PV have also been carried out as described in the Examples.

Recombinant Conformed Capsid Proteins as Immunogens

Subunit vaccines, based on self-assembled major capsid proteins synthesized in heterologous cells, have been proved effective in preventing infections by several pathogenic viruses, including human hepatitis B (Stevens, C., et al., Studies demonstrating that infectious or formalin inactivated BPV is effective as a vaccine, while BPV transformed cells are ineffective, suggest that viral capsid proteins, rather than early gene products, elicit the immune response. Other data in the scientific literature indicates that L1 protein extracted from bacteria was partially successful in eliciting an immune response despite the low titers of neutralizing antibodies. Accordingly, the BPV L1 that was expressed and assembled into virus-like particles in insect cells was studied for its ability to induce neutralizing antisera in rabbits. Two types of preparations were tested: whole cell extracts of L1 recombinant or wild type infected Sf-9 cells and partially purified particles isolated by differential centrifugation and ammonium sulfate precipitation. Following a primary inoculation, the rabbits received two biweekly booster inoculations.

Figure 3:
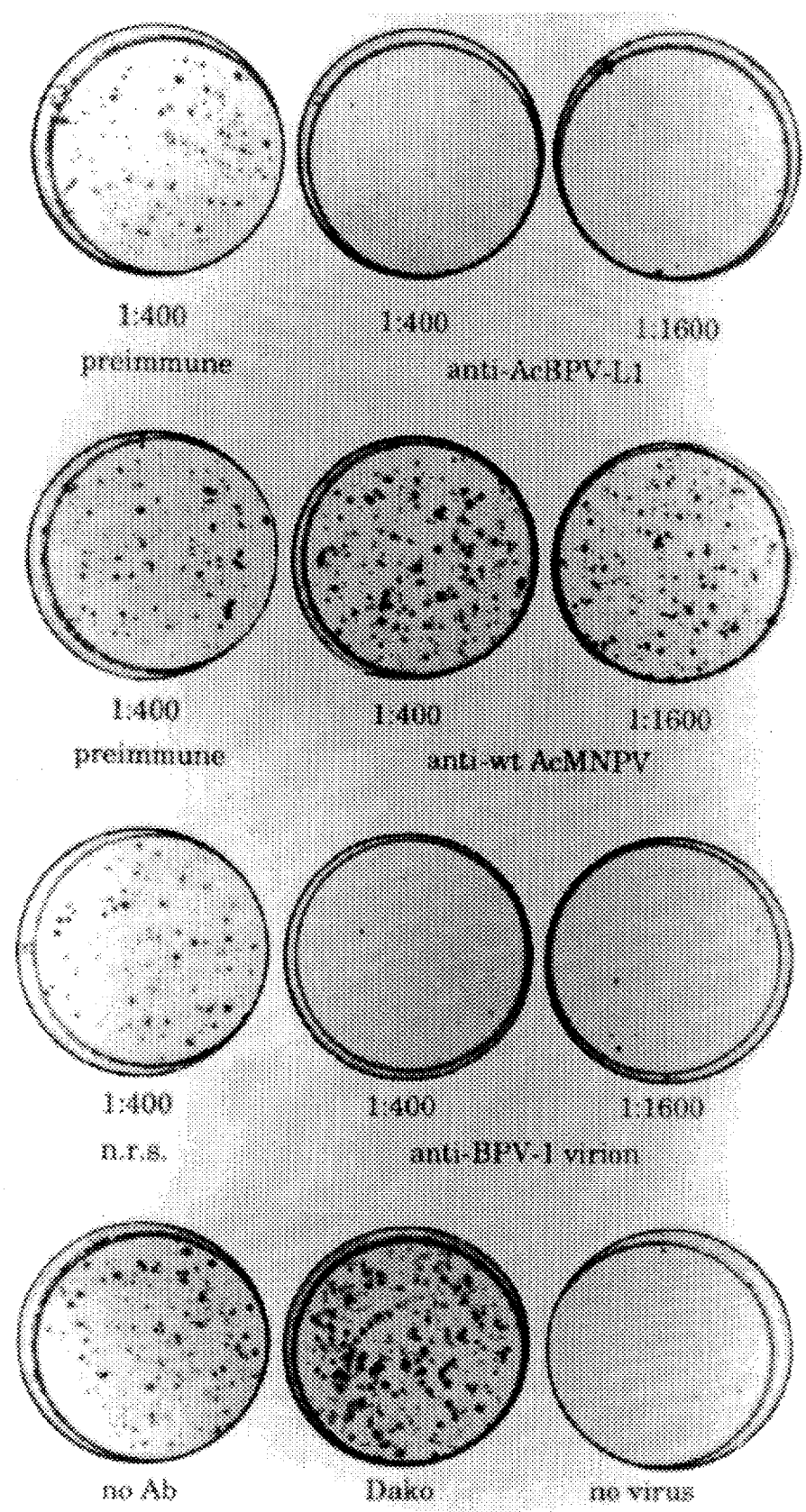
FIG. 3 shows the titers of neutralizing antisera induced in animals inoculated with recombinant BPV L1 as compared to antisera against intact and denatured BPV virions.

The rabbit sera were tested for the ability to inhibit BPV infection of mouse C127 cells, as measured by a reduction in the number of foci induced by a standard amount of BPV virus (a representative assay is shown in FIG. 3). The immune sera generated by inoculation with baculovirus derived L1 were able to reduce the infectivity of the BPV virus by 50% at a dilution of at least 1:11,000 (a titer of 11,000; Table 1), whereas the preimmune sera from the same rabbits did not inhibit focal transformation at a dilution of 1:20, the lowest dilution tested. Both the crude preparations and partially purified particles were effective in inducing high titer neutralizing antisera, with 290,000 being the highest titer measured. This was the same as the neutralizing titer of the positive control antiserum raised against infectious BPV virions. In comparison, the highest titer generated in a previous study using bacterially derived L1 was 36 (Pilancinski, W., et al., 1984). The serum from the rabbit inoculated with the extract from the wild type baculovirus infected cells was unable to inhibit infectivity at a dilution of 1:20, indicating that the neutralizing activity was L1 specific. Disruption of the partially purified L1 particles, by boiling in 1% SDS, abolished the ability of the preparation to induce neutralizing antibodies (Table 1). The demonstration that L1 can self-assemble into virion-like particles that elicit neutralizing antisera titers at least three orders of magnitude higher than previous in vitro-produced antigens suggests the recombinant L1 capsid proteins has the potential to induce effective long term protection against naturally transmitted papillomavirus. In view of these results, it appears that the L1 particles assembled in insect cells mimic infectious virus in the presentation of conformationally dependent immunodominant epitopes. These results also establish that L2 is not required for the generation of high titer neutralizing antibodies. The reported weak neutralizing immunogenicity of bacterially derived L1 may occur because it does not assume an appropriate conformation or has not assembled into virion like structures. Also, multiple electrophoretic variants of L1 have been detected in virions (Larsen, P., et al., 1987). Some of these modified species, which are probably absent in the bacterially derived L1, may facilitate the generation of neutralizing antibodies.

The ability of recombinant L1 (or L2) papillomavirus capsid proteins such as those disclosed herein to induce high titer neutralizing antiserum makes them suitable for use as vaccines for prophylaxis against communicable papillomatosis. Examples of populations at risk that could benefit from immunization are bovine herds, which are susceptible to papilloma warts; all humans for non-genital types of HPV infection; and sexually active humans for genital HPV types of infection.

Therapeutic vaccination can be useful for productive papillomavirus lesions, which usually express L1 (and L2) capsid proteins. Such lesions are most likely to occur in benign infections, such as warts or laryngeal papillomatosis. Laryngeal papillomatosis in newborns is usually contracted by the infant during passage through the birth canal where infectious papillomavirus is present in vaginal secretions. Therapeutic vaccination of infected pregnant women against the papillomavirus can induce neutralizing IgG antibody capable of passing through the placental barrier and into the circulation of the fetus to provide prophylactic passive immunity in the infant against this type of papillomavirus infection. Additional infant-protecting mechanisms are provided by maternal IgA which is secreted into the vaginal fluid and into breast milk. Jarrett (1991) demonstrates some therapeutic efficacy for L2 in treating BPV-induced warts. Malignant tumors typically do not express L1 or L2, and the efficacy of vaccination with recombinant L1 or L2 in conditions such as cervical cancer, is uncertain.

Protective immunity against both benign and malignant papillomavirus disease can be induced by administering an effective amount of recombinant L1 capsid protein to an individual at risk for papillomavirus infection. A vaccine comprising the capsid protein can be directly administered, either parenterally or locally, according to conventional immunization protocols. In an alternative embodiment, the conformational coding sequence of L1 can be cloned into a transfer vector, for example, a semliki forest virus vector (which produces a mild transient infection), the recombinant virus introduced into the cells or tissues of the recipient where the immunizing capsid protein is then expressed. Vaccinia virus can also be used as a vehicle for the gene.

Recombinant Conformed Capsid Proteins as Serological Screening Agents

Published serologic studies of human immune response to papillomavirus virion proteins have principally utilized bacterially derived L1 and L2 capsid proteins, and the results have not correlated well with other measures of HPV infection (Jenison, S., et al., 1990). BPV papillomavirus immunity studies described above indicate that papillomavirus virion proteins extracted from bacteria do not present the conformationally dependent epitopes that appear to be type-specific and recognized by most neutralizing antibodies. Compared with such assays that primarily recognize linear epitopes, a serological test using self-assembled L1 particles is likely to be a more accurate measure of the extent of anti-HPV virion immunity in the human population. The recombinant L1 capsid proteins disclosed herein, presenting conformational epitopes, can therefore be used as highly specific diagnostic reagents to detect immunity conferring neutralizing antibody to papilloma virus in binding assays of several types. The procedures can be carried out generally as either solid phase or solution assays that provide a means to detect antibodies in bodily fluids that specifically bind to the capsid protein in antigen-antibody pairs. Examples of procedures known to those skilled in the art for evaluating circulating antibodies are solution phase assays, such as double-antibody radioimmunoassays or enzyme immunoassays, or solid phase assays such as strip radioimmunoassay based on Western blotting or an enzyme-linked immunoabsorbent assay (ELISA) as disclosed in U.S. Pat. No. 4,520,113 to Gallo et al., or immunochromatographic assays as disclosed in U.S. Pat. No. 5,039,607 to Skold et al. A preferred ELISA method for the detection of antibodies is that disclosed in Harlow, E., and Lane, D. in *Antibodies: A Laboratory Manual* Cold Spring Harbor, NY, 1988, pp. 563–578.

The recombinant L1 or L1/L2 capsid proteins disclosed herein can also be used to measure cellular immunity to papillomavirus by means of in vivo or in vitro assays, for example, antigen-induced T-cell proliferative responses as described by Bradley, L., 1980, and particularly cellular responses to viral antigens, as described in U.S. Pat. No. 5,081,029 to Starling. Cellular immunity to papillomavirus can also be determined by the classical in vivo delayed hypersensitivity skin test as described by Stites, D., 1980; or in a preferred method, according to Höpfl, R., et al., 1991, by the intradermal injection of recombinant HPV L1 fusion proteins.

The capsid proteins of the invention can also be used as immunogens to raise polyclonal or monoclonal antibodies, according to methods well known in the art. These papillomavirus-specific .antibodies, particularly in combination with labelled second antibodies, specific for a class or species of antibodies, can be used diagnostically according to various conventional assay procedures, such as immunohistochemistry, to detect the presence of capsid proteins in samples of body tissue or bodily fluids.

The genetic manipulations described below are disclosed in terms of their general application to the preparation of elements of the genetic regulatory unit of the invention. Occasionally, the procedure may not be applicable as described to each recombinant molecule included within the disclosed scope. The situations for which this occurs will be readily recognized by those skilled in the art. In all such cases, either the operations can be successfully performed by conventional modifications known to those skilled in the art, e.g. by choice of an appropriate alternative restriction enzyme, by changing to alternative conventional reagents, or by routine modification of reaction conditions. Alternatively, other procedures disclosed herein or otherwise conventional will be applicable to the preparation of the corresponding recombinant molecules of the invention. In all preparative methods, all starting materials are known or readily preparable from known starting materials. In the following examples, all temperatures are set forth in degrees Celsius; unless otherwise indicated, all parts and percentages are by weight.

Without further elaboration, it is believed that one skilled in the art can, using the preceding description, utilize the invention to its fullest extent. The following preferred embodiments are therefore to be construed as merely illustrative and not limiting the remainder of the disclosure in any way whatsoever.

EXAMPLE 1

Full length L1, or L1 and L2 open reading frames (ORF) were amplified by PCR using the cloned prototypes of BPV1 DNA (Chen, E., et al., 1982), GertBank Accession No. X02346 or HPV16 DNA (Seedorf, K., et al., 1985), GenBankAccession No. K02718; or wild type HPV16 DNA (Sequence ID No. 2) as templates. Unique restriction sites were incorporated into the oligonucleotide primers (underlined).

BPV1-L1 primer sequence (Sequence ID No. 3):

5'-CCGCTGAATTCAATATGGCGTTGTGGCAACAA-GGCCAGAAGCTGTAT-3' (sense)

and (Sequence ID No. 4):

5'-GCGGTGGTACCGTGCAGTTGACTTACCTTCT-GTTTTACATTTACAGA-3' (antisense);

HPV16-L1 primer sequence (Sequence ID No. 5):

5'-CCGCTAGATCTAATATGTCTCTTTGGCTGCCT-AGTGAGGCC-3' (sense); and (Sequence ID No. 6):

5'-GCGGTAGATCTACACTAATTCAACATACATAC-AATACTTACAGC-3' (antisense).

L1 coding sequences begin at the 1st methionine codon (bold) for BPV1 and the 2nd methionine for HPV16. BPV1-L1 was cloned as a 5'-EcoRI to 3'-KpnI fragment and HPV16-L1 as a 5'-BglII to 3'-BglII fragment into the multiple cloning site downstream of the polyhedrin promoter of the AcMNPV based baculovirus transfer vector pEV mod (Wang, X., et al. 1991) and verified by sequencing through the AcMNPV/L1 junction. A quantity of 2 µg of CsCl-purified recombinant plasmid was cotransfected with 1 µg wild type AcMNPV DNA (Invitrogen, San Diego, California) into Sf-9 cells (ATCC) using lipofectin (Gibco/BRL, Gaithersburg, Md.) (Hartig, P., et al., 1991) and the recombinant baculoviruses plaque-purified as described (Summers, M., et al., 1987).

EXAMPLE 2

Expression of L1 Proteins or L1/L2 proteins in Insect Cells

Sf-9 cells were either mock infected (mock) or infected at a multiplicity of infection of 10 with either wt AcMNPV (wt) or AcBPV-L1 (B-L1), AcHPV16-L1 (16-nl), or AcHPV16-L1 (16-L1) and AcHPV16-L2 (16-L2) recombinant virus. After 72 hours, cells were lysed by boiling in Laemmli buffer and the lysates subjected to SDS-PAGE in 10% gels. Proteins were either stained with 0.25% Coomassie blue (FIG. 1A) or immunoblotted and probed with BPV LlmAbAU-1 (Nakai, Y., et al., 1986)(FIG. 1B) or HPV16L1 mAb CAMVIR-1 (McLean, C., et al., 1990)(FIG. 1C) and $^{125}$I-labeled Fab anti-mouse IgG (Amersham). P designates polyhedrin protein.

EXAMPLE 3

Production of antisera

Rabbits were immunized by subcutaneous injection either with whole cell Sf-9 lysates ($3\times10^7$ cells) prepared by one freeze/thaw cycle and 20×dounce homogenization (rabbit #1,2, and 8) or with 200 µg of L1 protein partially purified by differential centrifugation and 35% ammonium sulfate precipitation (#3,4,6, and 7), in complete Freund's adjuvant, and then boosted twice at two week intervals, using the same preparations in incomplete Freund's adjuvant.

EXAMPLE 4

Purification of Particles and Transmission Electron Microscopic (EMK) Analysis 500 ml of Sf-9 cells ($2\times10^6$/ml) were infected with AcBPV-L1 (FIG. 2A) or AcHPV16-L1 (FIG. 2C) or AcHPV16-L1/L2 (16-L1/L2) recombinant baculoviruses. After 72 hr, the harvested cells were sonicated in PBS for 60 sec. After low speed clarification, the lysates were subjected to centrifugation at 110,000g for 2.5 hr through a 40% (wt/vol) sucrose/PBS cushion (SW-28). The resuspended pellets were centrifuged to equilibrium at 141,000g for 20 hr at room temperature in a 10–40% (wt/wt) CsCl/PBS gradient. Fractions were harvested from the bottom and analyzed by SDS-PAGE. Immunoreactive fractions were dialyzed against PBS, concentrated by Centricon 30 (Millipore) ultrafiltration, and (for HPV16-L1) pelleted by centrifugation for 10 min at 30 psi in a A-100 rotor in an airfuge (Beckman). BPV1 virions (FIG. 2B) were purified from a bovine wart (generously provided by A. B. Jenson) as described (Cowseft, L., et al., 1987). Purified particles were adsorbed to carbon coated TEM grids, stained with 1% uranyl acetate and examined with a Philips electron microscope EM 400T at 36,000×magnification. Results are shown in FIG. 2. [The bar=50 nm ].

EXAMPLE 5

BPV1 neutralization assay

Serial dilutions of sera obtained 3 wk after the second boost were incubated with approximately 500 focus forming units of BPV1 virus for 30 min, the virus absorbed to C127 cells for 1 hr and the cells cultured for 3 weeks (Dvoretzky, I., et al., 1980). The foci were stained with 0.5% methylene blue/0.25% carbol fuchsin/methanol. The results are shown in FIG. 3 and are discussed below. The antisera and dilutions used are indicated below the plates. Anti-AcBPV-L1 was obtained from rabbit #1 and anti-wt AcMNPV from rabbit #8 (Table 1). The normal rabbit serum negative control is designated "nrs"; anti-BPV-1 virion was raised against native BPV virions in a previous study (Nakai, Y., et al., 1986); and Dako is the commercially available (Dako Corp, Santa Barbara, Calif.) rabbit antiserum raised against denatured BPV virions.

EXAMPLE 6

Serum Neutralizing Titer against BPV1

Assays were carried out as in Example 5. Rabbits #1, 2, and 8 were inoculated with crude whole cell Sf-9 lysates, and rabbits #3,4,6, and 7 with partially purified L1 protein (Table 1). Rabbits #6 and 7 were immunized with L1 protein preparations that had been denatured by boiling in 1% SDS. At least two bleeds, taken 3–6 weeks after the second boost, were tested for each rabbit and found to have the same titer. The titer of the preimmune sera from each of the rabbits was less than 20, the lowest dilution tested.

TABLE 1

| rabbit | | serum neutralization titer against BPV1* |
|---|---|---|
| AcBPV-L1 | 1 | 11,000 |
| " | 2 | 97,000 |
| " | 3 | 290,000 |
| " | 4 | 97,000 |
| BPV1-virions† | 5 | 290,000 |
| AcBPV-L1/SDS | 6 | <2 |
| " | 7 | <2 |
| wt AcMNPV | 8 | <20 | reciprocal of dilution that caused 50% focus reduction
†provided by A. B. Jenson (Nakai, Y., et al., 1986).

The invention may be embodied in other specific forms without departing from its spirit or essential characteristics. The described embodiments are to be considered in all respects only as illustrative and not restrictive, and the scope of the invention is, therefore, indicated by the appended claims rather than by the foregoing description. All modifications which come within the meaning and range of the lawful equivalency of the claims are to be embraced within their scope.

BIBLIOGRAPHY

U.S. Pat. No. 5,081,029 to Starling et al.

U.S. Pat. No. 5,039,607 to Skold et al.

U.S. Pat. No. 4,520,113 to Gallo et al.

Baker, C. in *The papovaviridae:* Vol.2. *The Papillomaviruses* (N. Salzman et al., eds.) Plenum Press, New York, 1987. p.321.

Baker, T., et al. Biophys. J. 60:1445 (1991).

Bradley, L. et al. in Selected Methods in Cellular Immunology. B. Mishell and S. Shiigi, eds. San Francisco: W. H. Freeman and Co., 1980. pp. 164–166.

Christensen, N., et al. Virology 64:5678 (1990).

Christensen, N., et al. Virology 181:572 (1991).

Crawford, L., et al. Virology 21:258 (1963).

Dvoretzky, I., et al. Virology 103:369 (1980).

Ghim, S., et al. Comparison of neutralization of BPV-1 infection of C127 cells and bovine fetal skin xenografts. Int. J. Cancer 49:285 (1991).

Ghim, S., et al. HPV1-L1 protein expressed in cos cells displays conformational epitopes found on intact virions. Virology 190:548–552 (1992).

Hagensee, M., et al. Self-assembly of human papillomavirus type 1 capsids by expression of the L1 protein alone or by coexpression of the L1 and L2 capsid proteins. J. of Virology 67(1):315–322.

Höpfl, R., et al. Skin test for HPV type 16 proteins in cervical intraepithelial neoplasia. Lancet 337:373 (1991).

Jarrett, W., et al. Veterinary Record 126:449 (1990).

Jarrett, W., et al. Studies on vaccination against papillomaviruses: prophylactic and therapeutic vaccination with recombinant structural proteins. Virology 184:33 (1991).

Jenison, S., et al. J. Infectious Dis. 162:60 (1990).

Jenson, A., et al. Identification of linear epitopes BPV-1 L1 protein recognized by sera of infected or immunized animals. Pathobiology 59:396 (1991)

Jin, X., et al. J. Gen. Virology 70:1133 (1989).

Kajigaya, S., et al. Proc. Natl. Acad. Sci. USA 88:4646 (1991).

Kirnbauer, R., et al. Papillomavirus L1 major capsid protein self-assembles into virus-like particles that are highly immunogenic. Proc. Natl. Acad. Sci. USA 89:12180–12184 (1992).

Larsen, P., et al. J. Virology 61:3596 (1987).

Liddington, R., et al. Nature 354:278 (1991).

Lin, Y-L., et al. Effective vaccination against papilloma development by immunization with L1 or L2 structural protein of cottontail rabbit papillovirus. Virology 187:612 (1992).

McLean, C., et al. Production and characterization of a monoclonal antibody to human papillomavirus type 16 using recombinant vaccinia virus. J. Clin. Pathol 43:488 (1990).

Nakai, Y. Intervirol. 25:30 (1986).

Olson, C., et al. Amer. J. Vet. Res. 21:233 (1960).

Pilacinski, W., et al. Biotechnology 2:356 (1984).

Saiki, R. K., et al. Science 239:487 (1987).

Seedorf, et al. Human papillomavirus type 16 DNA sequence. Virology 145:181–185 (1985)

Shiffman, M. J. National Cancer Inst. 84:394 (1992).

Stevens, C., et al. JAMA 257:2612 (1987).

Stites, D. Chapter 27 in *Basic and Clinical Immunology* 3rd Ed. H. Fudenberg et al., eds. Los Altos: Lange Medical Publications, 1980.

Summers, M., et al. Texas Agricultural Experiment Station, College Station, Texas. A Manual of Methods for Baculovirus Vectors and Insect Cell Culture Procedures (1987). Bulletin No. 1555.

Zhou, J., et al. Expression of vaccinia recombinant HPV 16 L1 and L2ORF proteins in epithelial cells is sufficient for assembly of HPV virion-like particles. J. Virology 185:251 (1991).

zur Hausen, H. Science 254:1167 (1991).

---

What is claimed is:

1. A unit dose of immunogenic composition comprising a self-assembled HPV16 papillomavirus-like particle comprising at least one papillomavirus L1 conformational epitope produced by the method comprising the step g of:

permitting a genetic construct, comprising a papillomavirus L1 gene, to direct recombinant expression in a transformed eukaryotic host cell of said papillomavirus L1 conformational epitope by self-assembly of papillomavirus-like particles comprising a L1 polypeptide, wherein said L1 polypeptide is characterized as having the amino acid sequence encoded by the nucleotide sequence of SEQ ID NO:2, said unit dose being in an effective immunogenic concentration sufficient to induce a papillomavirus neutralizing antibody titer of at least about $10^3$ when administered according to an immunizing dosage schedule.

2. The unit dose of claim 1, wherein said L1 gene comprises the nucleotide sequence of SEQ ID NO:2.

3. The unit dose of claim 1, wherein said papillomavirus-like particles further comprise a L2 polypeptide, and wherein recombinant expression of said L2 polypeptide is directed either by said construct further comprising a papillomavirus L2 gene or a different genetic construct comprising a papillomavirus L2 gene.

4. The unit dose of claim 3, wherein said construct further comprises said papillomavirus L2 gene.

5. The unit dose of claim 1, wherein said construct further comprises an insect cell vector, and wherein said host cell is an insect cell host.

6. The unit dose of claim 5, wherein said insect cell vector is a baculovirus vector and said insect cell host is a Sf-9 insect cell.

7. The unit dose of claim 6, wherein said baculovirus vector is formed by cotransfecting an Sf-9 insect cell with recombinant baculovirus DNA and wild-type baculovirus DNA.

8. The unit dose of claim 1, wherein said construct further comprises a mammalian cell vector, and wherein said host cell is a mammalian cell host.

9. The unit dose of claim 8, wherein said mammalian cell vector is a vaccinia vector.

10. The unit dose of claim 1, wherein said construct further comprises a yeast cell vector, and wherein said host cell is a yeast cell host.

11. A unit dose of immunogenic composition comprising a self-assembled HPVI 6 papillomavirus-like particle comprising at least one papillomavirus L1 conformational epitope produced by the method comprising the step of:

permitting a genetic construct, comprising a papillomavirus L1 gene, to direct recombinant expression in a transformed eukaryotic host cell of said papillomavirus L1 conformational epitope by self-assembly of papillomavirus-like particles ("VLPs") comprising a L1 polypeptide, with the proviso that said VLPs do not contain a L2 polypeptide, wherein said L1 polypeptide is characterized as having the amino acid sequence encoded by the nucleotide sequence of SEQ ID NO:2, said unit dose being in an effective immunogenic concentration sufficient to induce a papillomavirus neutralizing antibody titer of at least about $10^3$ when administered according to an immunizing dosage schedule.

12. The unit dose of claim 11, wherein said L1 gene comprises the nucleotide sequence of SEQ ID NO:2.

* * * * *

UNITED STATES PATENT AND TRADEMARK OFFICE
CERTIFICATE OF CORRECTION

PATENT NO. : 5,716,620
DATED : February 10, 1998
INVENTOR(S) : Lowy, et al.

It is certified that error appears in the above-indentified patent and that said Letters Patent is hereby corrected as shown below:

Column 25, line 62 "step g of:" should be --step of:--

Column 28, line 2 "HPVI 6" should be --HPV16--

Signed and Sealed this

Twenty-eighth Day of July, 1998

Attest:

BRUCE LEHMAN

Attesting Officer     Commissioner of Patents and Trademarks

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 1517 base pairs
( B ) TYPE: nucleic acid (C) STRANDEDNESS: single
(D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Human papillomavirus
    (B) STRAIN: HPV16

(ix) FEATURE:
    (A) NAME/KEY: CDS
    (B) LOCATION: 1..1517

(xi) SEQUENCE DESCRIPTION: SEQ ID NO:1:

```
ATG TCT CTT TGG CTG CCT AGT GAG GCC ACT GTC TAC TTG CCT CCT GTC          48
Met Ser Leu Trp Leu Pro Ser Glu Ala Thr Val Tyr Leu Pro Pro Val
 1           5                  10                  15

CCA GTA TCT AAG GTT GTA AGC ACG GAT GAA TAT GTT GCA CGC ACA AAC          96
Pro Val Ser Lys Val Val Ser Thr Asp Glu Tyr Val Ala Arg Thr Asn
             20                  25                  30

ATA TAT TAT CAT GCA GGA ACA TCC AGA CTA CTT GCA GTT GGA CAT CCC         144
Ile Tyr Tyr His Ala Gly Thr Ser Arg Leu Leu Ala Val Gly His Pro
         35                  40                  45

TAT TTT CCT ATT AAA AAA CCT AAC AAT AAC AAA ATA TTA GTT CCT AAA         192
Tyr Phe Pro Ile Lys Lys Pro Asn Asn Asn Lys Ile Leu Val Pro Lys
     50                  55                  60

GTA TCA GGA TTA CAA TAC AGG GTA TTT AGA ATA CAT TTA CCT GAC CCC         240
Val Ser Gly Leu Gln Tyr Arg Val Phe Arg Ile His Leu Pro Asp Pro
 65                  70                  75                  80

AAT AAG TTT GGT TTT CCT GAC ACC TCA TTT TAT AAT CCA GAT ACA CAG         288
Asn Lys Phe Gly Phe Pro Asp Thr Ser Phe Tyr Asn Pro Asp Thr Gln
                 85                  90                  95

CGG CTG GTT TGG GCC TGT GTA GGT GTT GAG GTA GGT CGT GGT CAG CCA         336
Arg Leu Val Trp Ala Cys Val Gly Val Glu Val Gly Arg Gly Gln Pro
            100                 105                 110

TTA GGT GTG GGC ATT AGT GGC CAT CCT TTA TTA AAT AAA TTG GAT GAC         384
Leu Gly Val Gly Ile Ser Gly His Pro Leu Leu Asn Lys Leu Asp Asp
        115                 120                 125

ACA GAA AAT GCT AGT GCT TAT GCA GCA AAT GCA GGT GTG GAT AAT AGA         432
Thr Glu Asn Ala Ser Ala Tyr Ala Ala Asn Ala Gly Val Asp Asn Arg
    130                 135                 140

GAA TGT ATA TCT ATG GAT TAC AAA CAA ACA CAA TTG TGT TTA ATT GGT         480
Glu Cys Ile Ser Met Asp Tyr Lys Gln Thr Gln Leu Cys Leu Ile Gly
145                 150                 155                 160

TGC AAA CCA CCT ATA GGG GAA CAC TGG GGC AAA GGA TCC CCA TGT ACC         528
Cys Lys Pro Pro Ile Gly Glu His Trp Gly Lys Gly Ser Pro Cys Thr
                165                 170                 175

AAT GTT GCA GTA AAT CCA GGT GAT TGT CCA CCA TTA GAG TTA ATA AAC         576
Asn Val Ala Val Asn Pro Gly Asp Cys Pro Pro Leu Glu Leu Ile Asn
            180                 185                 190

ACA GTT ATT CAG GAT GGT GAT ATG GTT CAT ACT GGC TTT GGT GCT ATG         624
Thr Val Ile Gln Asp Gly Asp Met Val His Thr Gly Phe Gly Ala Met
        195                 200                 205

GAC TTT ACT ACA TTA CAG GCT AAC AAA AGT GAA GTT CCA CTG GAT ATT         672
Asp Phe Thr Thr Leu Gln Ala Asn Lys Ser Glu Val Pro Leu Asp Ile
    210                 215                 220

TGT ACA TCT ATT TGC AAA TAT CCA GAT TAT ATT AAA ATG GTG TCA GAA         720
Cys Thr Ser Ile Cys Lys Tyr Pro Asp Tyr Ile Lys Met Val Ser Glu
225                 230                 235                 240

CCA TAT GGC GAC AGC TTA TTT TTT TAT TTA CGA AGG GAA CAA ATG TTT         768
```

```
Pro Tyr Gly Asp Ser Leu Phe Phe Tyr Leu Arg Arg Glu Gln Met Phe
            245                 250                 255

GTT AGA CAT TTA TTT AAT AGG GCT GGT ACT GTT GGT GAA AAT GTA CCA      816
Val Arg His Leu Phe Asn Arg Ala Gly Thr Val Gly Glu Asn Val Pro
            260                 265                 270

GAC GAT TTA TAC ATT AAA GGC TCT GGG TCT ACT GCA AAT TTA GCC AGT      864
Asp Asp Leu Tyr Ile Lys Gly Ser Gly Ser Thr Ala Asn Leu Ala Ser
            275                 280                 285

TCA AAT TAT TTT CCT ACA CCT AGT GGT TCT ATG GTT ACC TCT GAT GCC      912
Ser Asn Tyr Phe Pro Thr Pro Ser Gly Ser Met Val Thr Ser Asp Ala
        290                 295                 300

CAA ATA TTC AAT AAA CCT TAT TGG TTA CAA CGA GCA CAG GGC CAC AAT      960
Gln Ile Phe Asn Lys Pro Tyr Trp Leu Gln Arg Ala Gln Gly His Asn
305                 310                 315                 320

AAT GGC ATT TGT TGG GGT AAC CAA CTA TTT GTT ACT GTT GTT GAT ACT     1008
Asn Gly Ile Cys Trp Gly Asn Gln Leu Phe Val Thr Val Val Asp Thr
            325                 330                 335

ACA CGC AGT ACA AAT ATG TCA TTA TGT GCT GCC ATA TCT ACT TCA GAA     1056
Thr Arg Ser Thr Asn Met Ser Leu Cys Ala Ala Ile Ser Thr Ser Glu
            340                 345                 350

ACT ACA TAT AAA AAT ACT AAC TTT AAG GAG TAC CTA CGA CAT GGG GAG     1104
Thr Thr Tyr Lys Asn Thr Asn Phe Lys Glu Tyr Leu Arg His Gly Glu
            355                 360                 365

GAA TAT GAT TTA CAG TTT ATT TTT CAA CTG TGC AAA ATA ACC TTA ACT     1152
Glu Tyr Asp Leu Gln Phe Ile Phe Gln Leu Cys Lys Ile Thr Leu Thr
        370                 375                 380

GCA GAC GTT ATG ACA TAC ATA CAT TCT ATG AAT TCC ACT ATT TTG GAG     1200
Ala Asp Val Met Thr Tyr Ile His Ser Met Asn Ser Thr Ile Leu Glu
385                 390                 395                 400

GAC TGG AAT TTT GGT CTA CAA CCT CCC CCA GGA GGC ACA CTA GAA GAT     1248
Asp Trp Asn Phe Gly Leu Gln Pro Pro Pro Gly Gly Thr Leu Glu Asp
            405                 410                 415

ACT TAT AGG TTT GTA ACA TCC CAG GCA ATT GCT TGT CAA AAA CAT ACA     1296
Thr Tyr Arg Phe Val Thr Ser Gln Ala Ile Ala Cys Gln Lys His Thr
            420                 425                 430

CCT CCA GCA CCT AAA GAA GAT CCC CTT AAA AAA TAC ACT TTT TGG GAA     1344
Pro Pro Ala Pro Lys Glu Asp Pro Leu Lys Lys Tyr Thr Phe Trp Glu
            435                 440                 445

GTA AAT TTA AAG GAA AAG TTT TCT GCA GAC CTA GAT CAG TTT CCT TTA     1392
Val Asn Leu Lys Glu Lys Phe Ser Ala Asp Leu Asp Gln Phe Pro Leu
450                 455                 460

GGA CGC AAA TTT TTA CTA CAA GCA GGA TTG AAG GCC AAA CCA AAA TTT     1440
Gly Arg Lys Phe Leu Leu Gln Ala Gly Leu Lys Ala Lys Pro Lys Phe
465                 470                 475                 480

ACA TTA GGA AAA CGA AAA GCT ACA CCC ACC ACC TCA TCT ACC TCT ACA     1488
Thr Leu Gly Lys Arg Lys Ala Thr Pro Thr Thr Ser Ser Thr Ser Thr
            485                 490                 495

ACT GCT AAA CGC AAA AAA CGT AAG CTG TA                              1517
Thr Ala Lys Arg Lys Lys Arg Lys Leu
            500                 505
```

( 2 ) INFORMATION FOR SEQ ID NO:2:

( i ) SEQUENCE CHARACTERISTICS:
        ( A ) LENGTH: 1517 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
    ( A ) NAME/KEY: CDS
    ( B ) LOCATION: 1..1517

( x i ) SEQUENCE DESCRIPTION: SEQ ID NO:2:

```
ATG TCT CTT TGG CTG CCT AGT GAG GCC ACT GTC TAC TTG CCT CCT GTC      48
Met Ser Leu Trp Leu Pro Ser Glu Ala Thr Val Tyr Leu Pro Pro Val
 1               5                  10                  15

CCA GTA TCT AAG GTT GTA AGC ACG GAT GAA TAT GTT GCA CGC ACA AAC      96
Pro Val Ser Lys Val Val Ser Thr Asp Glu Tyr Val Ala Arg Thr Asn
             20                  25                  30

ATA TAT TAT CAT GCA GGA ACA TCC AGA CTA CTT GCA GTT GGA CAT CCC     144
Ile Tyr Tyr His Ala Gly Thr Ser Arg Leu Leu Ala Val Gly His Pro
                 35                  40                  45

TAT TTT CCT ATT AAA AAA CCT AAC AAT AAC AAA ATA TTA GTT CCT AAA     192
Tyr Phe Pro Ile Lys Lys Pro Asn Asn Asn Lys Ile Leu Val Pro Lys
     50                  55                  60

GTA TCA GGA TTA CAA TAC AGG GTA TTT AGA ATA CAT TTA CCT GAC CCC     240
Val Ser Gly Leu Gln Tyr Arg Val Phe Arg Ile His Leu Pro Asp Pro
 65                  70                  75                  80

AAT AAG TTT GGT TTT CCT GAC ACC TCA TTT TAT AAT CCA GAT ACA CAG     288
Asn Lys Phe Gly Phe Pro Asp Thr Ser Phe Tyr Asn Pro Asp Thr Gln
                 85                  90                  95

CGG CTG GTT TGG GCC TGT GTA GGT GTT GAG GTA GGT CGT GGT CAG CCA     336
Arg Leu Val Trp Ala Cys Val Gly Val Glu Val Gly Arg Gly Gln Pro
                100                 105                 110

TTA GGT GTG GGC ATT AGT GGC CAT CCT TTA TTA AAT AAA TTG GAT GAC     384
Leu Gly Val Gly Ile Ser Gly His Pro Leu Leu Asn Lys Leu Asp Asp
            115                 120                 125

ACA GAA AAT GCT AGT GCT TAT GCA GCA AAT GCA GGT GTG GAT AAT AGA     432
Thr Glu Asn Ala Ser Ala Tyr Ala Ala Asn Ala Gly Val Asp Asn Arg
        130                 135                 140

GAA TGT ATA TCT ATG GAT TAC AAA CAA ACA CAA TTG TGT TTA ATT GGT     480
Glu Cys Ile Ser Met Asp Tyr Lys Gln Thr Gln Leu Cys Leu Ile Gly
145                 150                 155                 160

TGC AAA CCA CCT ATA GGG GAA CAC TGG GGC AAA GGA TCC CCA TGT ACC     528
Cys Lys Pro Pro Ile Gly Glu His Trp Gly Lys Gly Ser Pro Cys Thr
                165                 170                 175

AAT GTT GCA GTA AAT CCA GGT GAT TGT CCA CCA TTA GAG TTA ATA AAC     576
Asn Val Ala Val Asn Pro Gly Asp Cys Pro Pro Leu Glu Leu Ile Asn
                180                 185                 190

ACA GTT ATT CAG GAT GGT GAT ATG GTT GAT ACT GGC TTT GGT GCT ATG     624
Thr Val Ile Gln Asp Gly Asp Met Val Asp Thr Gly Phe Gly Ala Met
            195                 200                 205

GAC TTT ACT ACA TTA CAG GCT AAC AAA AGT GAA GTT CCA CTG GAT ATT     672
Asp Phe Thr Thr Leu Gln Ala Asn Lys Ser Glu Val Pro Leu Asp Ile
210                 215                 220

TGT ACA TCT ATT TGC AAA TAT CCA GAT TAT ATT AAA ATG GTG TCA GAA     720
Cys Thr Ser Ile Cys Lys Tyr Pro Asp Tyr Ile Lys Met Val Ser Glu
225                 230                 235                 240

CCA TAT GGC GAC AGC TTA TTT TTT TAT TTA CGA AGG GAA CAA ATG TTT     768
Pro Tyr Gly Asp Ser Leu Phe Phe Tyr Leu Arg Arg Glu Gln Met Phe
                245                 250                 255

GTT AGA CAT TTA TTT AAT AGG GCT GGT ACT GTT GGT GAA AAT GTA CCA     816
Val Arg His Leu Phe Asn Arg Ala Gly Thr Val Gly Glu Asn Val Pro
            260                 265                 270

GAC GAT TTA TAC ATT AAA GGC TCT GGG TCT ACT GCA AAT TTA GCC AGT     864
Asp Asp Leu Tyr Ile Lys Gly Ser Gly Ser Thr Ala Asn Leu Ala Ser
        275                 280                 285
```

```
TCA AAT TAT TTT CCT ACA CCT AGT GGT TCT ATG GTT ACC TCT GAT GCC      912
Ser Asn Tyr Phe Pro Thr Pro Ser Gly Ser Met Val Thr Ser Asp Ala
    290                 295                 300

CAA ATA TTC AAT AAA CCT TAT TGG TTA CAA CGA GCA CAG GGC CAC AAT      960
Gln Ile Phe Asn Lys Pro Tyr Trp Leu Gln Arg Ala Gln Gly His Asn
305                 310                 315                 320

AAT GGC ATT TGT TGG GGT AAC CAA CTA TTT GTT ACT GTT GTT GAT ACT     1008
Asn Gly Ile Cys Trp Gly Asn Gln Leu Phe Val Thr Val Val Asp Thr
                    325                 330                 335

ACA CGC AGT ACA AAT ATG TCA TTA TGT GCT GCC ATA TCT ACT TCA GAA     1056
Thr Arg Ser Thr Asn Met Ser Leu Cys Ala Ala Ile Ser Thr Ser Glu
            340                 345                 350

ACT ACA TAT AAA AAT ACT AAC TTT AAG GAG TAC CTA CGA CAT GGG GAG     1104
Thr Thr Tyr Lys Asn Thr Asn Phe Lys Glu Tyr Leu Arg His Gly Glu
        355                 360                 365

GAA TAT GAT TTA CAG TTT ATT TTT CAA CTG TGC AAA ATA ACC TTA ACT     1152
Glu Tyr Asp Leu Gln Phe Ile Phe Gln Leu Cys Lys Ile Thr Leu Thr
    370                 375                 380

GCA GAC GTT ATG ACA TAC ATA CAT TCT ATG AAT TCC ACT ATT TTG GAG     1200
Ala Asp Val Met Thr Tyr Ile His Ser Met Asn Ser Thr Ile Leu Glu
385                 390                 395                 400

GAC TGG AAT TTT GGT CTA CAA CCT CCC CCA GGA GGC ACA CTA GAA GAT     1248
Asp Trp Asn Phe Gly Leu Gln Pro Pro Pro Gly Gly Thr Leu Glu Asp
                    405                 410                 415

ACT TAT AGG TTT GTA ACC CAG GCA ATT GCT TGT CAA AAA CAT ACA CCT     1296
Thr Tyr Arg Phe Val Thr Gln Ala Ile Ala Cys Gln Lys His Thr Pro
            420                 425                 430

CCA GCA CCT AAA GAA GAT GAT CCC CTT AAA AAA TAC ACT TTT TGG GAA     1344
Pro Ala Pro Lys Glu Asp Asp Pro Leu Lys Lys Tyr Thr Phe Trp Glu
        435                 440                 445

GTA AAT TTA AAG GAA AAG TTT TCT GCA GAC CTA GAT CAG TTT CCT TTA     1392
Val Asn Leu Lys Glu Lys Phe Ser Ala Asp Leu Asp Gln Phe Pro Leu
    450                 455                 460

GGA CGC AAA TTT TTA CTA CAA GCA GGA TTG AAG GCC AAA CCA AAA TTT     1440
Gly Arg Lys Phe Leu Leu Gln Ala Gly Leu Lys Ala Lys Pro Lys Phe
465                 470                 475                 480

ACA TTA GGA AAA CGA AAA GCT ACA CCC ACC ACC TCA TCT ACC TCT ACA     1488
Thr Leu Gly Lys Arg Lys Ala Thr Pro Thr Thr Ser Ser Thr Ser Thr
                    485                 490                 495

ACT GCT AAA CGC AAA AAA CGT AAG CTG TA                              1517
Thr Ala Lys Arg Lys Lys Arg Lys Leu
            500                 505
```

(2) INFORMATION FOR SEQ ID NO:3:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Bovine papillomavirus (vii) IMMEDIATE SOURCE:
        (B) CLONE: BPV1 N (xi) SEQUENCE DESCRIPTION: SEQ ID NO:3:

```
CCGCTGAATT CAATATGGCG TTGTGGCAAC AAGGCCAGAA GCTGTAT                   47
```

(2) INFORMATION FOR SEQ ID NO:4:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vii) IMMEDIATE SOURCE:
        (B) CLONE: BPV1 Y (xi) SEQUENCE DESCRIPTION: SEQ ID NO:4:

```
GCGGTGGTAC CGTGCAGTTG ACTTACCTTC TGTTTACAT TTACAGA                47
```

(2) INFORMATION FOR SEQ ID NO:5:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vii) IMMEDIATE SOURCE:
        (B) CLONE: HPV16 N (xi) SEQUENCE DESCRIPTION: SEQ ID NO:5:

```
CCGCTAGATC TAATATGTCT CTTTGGCTGC CTAGTGAGGC C          41
```

(2) INFORMATION FOR SEQ ID NO:6:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: YES (vii) IMMEDIATE SOURCE:
        (B) CLONE: HPV16 Y (xi) SEQUENCE DESCRIPTION: SEQ ID NO:6:

```
GCGGTAGATC TACACTAATT CAACATACAT ACAATACTTA CAGC           44
```